(12) United States Patent
Gremminger et al.

(10) Patent No.: US 8,370,009 B2
(45) Date of Patent: Feb. 5, 2013

(54) SYSTEM, METHOD, AND COMPUTER PROGRAM PRODUCT FOR MONITORING OIL CONDITION

(75) Inventors: William Gremminger, Virginia Beach, VA (US); Emil Hasl, Virginia Beach, VA (US)

(73) Assignee: AB Volvo Penta, Gothenburg (SE)

( * ) Notice: Subject to any disclaimer, the term of this patent is extended or adjusted under 35 U.S.C. 154(b) by 389 days.

(21) Appl. No.: 12/635,157

(22) Filed: Dec. 10, 2009

(65) Prior Publication Data

US 2011/0144851 A1    Jun. 16, 2011

(51) Int. Cl.
*G06F 19/00* (2011.01)
(52) U.S. Cl. .......................................... 701/21; 701/29.5
(58) Field of Classification Search .................. 701/29.1, 701/29.5, 31.1, 34.4
See application file for complete search history.

(56) References Cited

U.S. PATENT DOCUMENTS

| | | | | |
|---|---|---|---|---|
| 3,042,146 A * | 7/1962 | Shimanckas | ................ | 184/6.18 |
| 4,794,897 A | 1/1989 | Kinouchi | | |
| 5,076,397 A * | 12/1991 | Yamada | ...................... | 184/108 |
| 5,642,098 A * | 6/1997 | Santa Maria et al. | ......... | 340/618 |
| 5,889,200 A * | 3/1999 | Centers et al. | .............. | 73/53.01 |
| 6,014,894 A * | 1/2000 | Herron | ........................ | 73/61.43 |
| 6,106,151 A | 8/2000 | Johannesson | | |
| 6,354,975 B1 * | 3/2002 | Thoma | .......................... | 475/83 |
| 6,459,995 B1 * | 10/2002 | Collister | ......................... | 702/23 |
| 6,617,968 B1 * | 9/2003 | Odisho et al. | ............. | 340/450.3 |
| 2004/0074469 A1 * | 4/2004 | Waters | ...................... | 123/198 F |
| 2008/0053217 A1 * | 3/2008 | Nishio et al. | .................. | 73/291 |

* cited by examiner

*Primary Examiner* — Dalena Tran
*Assistant Examiner* — Jason Holloway
(74) *Attorney, Agent, or Firm* — Michael Pruden; Martin Farrell (57) ABSTRACT

The present invention relates to a system, method, and computer program product for monitoring oil condition. In one embodiment, a marine powertrain is provided that includes a marine engine and a gear casing containing an oil and a gas. An engine speed sensor generates an output value, which indicates a speed of the marine engine. An oil sensor generates an output value, which indicates a condition of the oil. The condition of the oil is selectively monitored according to whether the marine engine is operating at a speed that is less than an engine speed threshold value, which denotes a speed of the marine engine at which the oil and the gas form an oil and aerated gas mixture.

16 Claims, 5 Drawing Sheets

SYSTEM, METHOD, AND COMPUTER PROGRAM PRODUCT FOR MONITORING OIL CONDITION

FIELD OF THE INVENTION

The present invention relates to a system, method, and computer program product for monitoring oil condition and particularly in a preferred form to a system, method, and computer program product for monitoring oil condition in a gear casing of a marine powertrain.

BACKGROUND OF THE INVENTION

Many mechanical devices use oil for lubrication purposes. In devices that use oil for lubrication purposes, it may be particularly important to periodically check the condition of the oil, such as, for example, the level and quality of the oil. Oil quality may change for a number of reasons, including as a result of oxidation, hydrolysis, thermal extremes, and the introduction of contaminants.

Marine powertrains are provided with what is commonly known as a lower unit or an outdrive, which extends below the water line. The lower unit or outdrive houses gears, which transfer power from the marine engine to a marine propulsion device, such as a propeller, provided on the lower unit or outdrive. The lower unit or outdrive also includes a gear casing that contains oil for lubrication of the gears.

It is a particular problem with marine powertrains that the oil in the lower unit or outdrive may become contaminated with water. Since the lower unit or outdrive sits below the water line during operation, the failure of a seal or the striking of an object may readily allow water to enter into the gear casing. Depending on the amount and duration of its presence, water within the gear casing may cause a number of undesirable consequences, including gear corrosion, increased gear and bearing wear due to a decrease in the effectiveness of the oil to act as a lubricant, complete gear failure, engine seizure, or a cracked lower unit or outdrive when the boat is removed from water and stored in cold weather climates. These consequences may translate into costly repairs or complete marine powertrain replacement.

One arrangement for checking the condition of oil involves using a conventional dip stick. While useful for checking the level and to a certain extent the quality of the oil, partially due to the fact that oil and water do not mix, it may not be possible to detect the presence of water by using a dip stick, particularly when the amount of water contamination is minimal.

Another arrangement for checking the condition of oil involves an oil reservoir located remotely from the gear casing and connected to the gear casing via conduits, such as hoses. The reservoir is typically placed in an easily accessible location such as near the marine engine of the marine powertrain and is typically made from a transparent material, such as plastic. Since the oil in the reservoir changes to a milky color in the presence of water, the presence of water may be visually detected from within the boat. Since in this arrangement the reservoir is positioned at an upper portion of the marine engine and the gear casing is located below the water line, gravity results in the gear casing becoming completely filled with oil. Completely filling the gear casing with oil increases the drag on the gears. This, in turn, decreases the efficiency of the power transfer from the marine engine to the marine propulsion device.

Yet another arrangement for monitoring the condition of oil involves the use of a variety of sensors, including, for example, capacitance sensors, optical sensors, or electrical resistance sensors. As just one example, since the dielectric constant of the oil is a function of the quality of the oil, those of ordinary skill in the art will appreciate that oil quality, including the presence of contaminants, such as water, may be determined by utilizing capacitance sensors to monitor the dielectric constant of the oil contained within the gear casing. Furthermore, those of ordinary skill in the art will appreciate that the capacitance sensor may be positioned so that in the event the oil level is below the position of the sensor, a dangerously low level of oil may be detected as well. Those of ordinary skill in the art will appreciate that capacitance sensors may monitor the dielectric constant in a number of ways, such as, for example, by outputting a voltage output, which varies according to the dielectric constant or by outputting an oscillating current frequency, which varies according to the dielectric constant. Regardless of the particular sensor employed, the sensor may be used in conjunction with a display or an alarm for indicating the oil condition or a problem with the oil condition.

Empirical analysis has demonstrated that in situations where the oil is contained in the gear casing along with a gas, such as air, i.e. in situations where the gear casing is not completely filled with oil, the oil and air may mix when the engine operates at high speeds to thereby create a foam-like mixture of oil that is aerated with gas. When this occurs, it may be difficult to reliably ascertain the condition of the oil using a variety of sensor technologies. As just one example, since the dielectric constant of the oil and gas mixture is different than the dielectric constant of liquid oil, making determinations of oil condition based on the dielectric constant of such a mixture may prove to be inaccurate. Empirical analysis has demonstrated that this oil and gas mixture phenomenon is acute according to the speed at which the marine engine is operated.

The present invention is directed toward an improved system, method, and computer program product for monitoring oil condition.

SUMMARY OF THE INVENTION

According to one aspect of the present invention, a system for monitoring oil condition comprises a marine powertrain, and engine speed sensor, an oil sensor, and one or more electronics. The marine powertrain is provided with a marine engine and a gear casing containing an oil and a gas. The engine speed sensor generates an output value, which indicates a speed of the marine engine. The oil sensor generates an output value, which indicates a condition of the oil. The one or more electronics receive the output value from the oil sensor, receive the output value from the engine speed sensor, and selectively monitor the condition of the oil according to whether the marine engine is operating at a speed that is less than an engine speed threshold value, which denotes a speed of the marine engine at which the oil and the gas form an oil and aerated gas mixture.

According to another aspect of the present invention, a method for monitoring oil condition comprises providing a marine powertrain that includes a marine engine and a gear casing containing an oil and a gas, using an engine speed sensor to generate an output value, which indicates a speed of the marine engine, using an oil sensor to generate an output value, which indicates a condition of the oil, comparing the output value generated by the engine speed sensor to an engine speed threshold value, which corresponds to a speed of the marine engine at which the oil and the gas form an oil and aerated gas mixture, and selectively monitoring the condition of the oil according to whether the marine engine is operating at a speed that is less than the engine speed threshold value.

According to yet another aspect of the present embodiment, a computer program product comprises computer usable medium including executable code for executing a process for monitoring oil condition in a marine powertrain, which includes a marine engine and a gear casing containing an oil and a gas, an engine speed sensor that generates an output value, which indicates a speed of the marine engine, and an oil sensor, which generates an output value indicating a condition of the oil, the process comprises the steps of comparing the output value generated by the engine speed sensor to an engine speed threshold value, which corresponds to a speed of the marine engine at which the oil and the gas form an oil and aerated gas mixture and selectively monitoring the condition of the oil according to whether the marine engine is operating at a speed that is less than the engine speed threshold value.

According to still yet another aspect of the present invention, a method for calibrating an oil sensor comprises the steps of providing a marine power train including an engine and gear casing that includes an oil sensor, wherein said oil sensor generates output values, which fluctuate according to a condition of oil in the gear casing, removing used oil located in the gear casing, introducing new oil into the gear casing and then using one or more of the oil sensor output values to establish a normative baseline corresponding to an acceptable oil condition and establishing one or more threshold values, which denote an unacceptable oil condition, by adding or subtracting from the normative baseline.

DETAILED DESCRIPTION OF THE PREFERRED EMBODIMENTS

Figure 1:
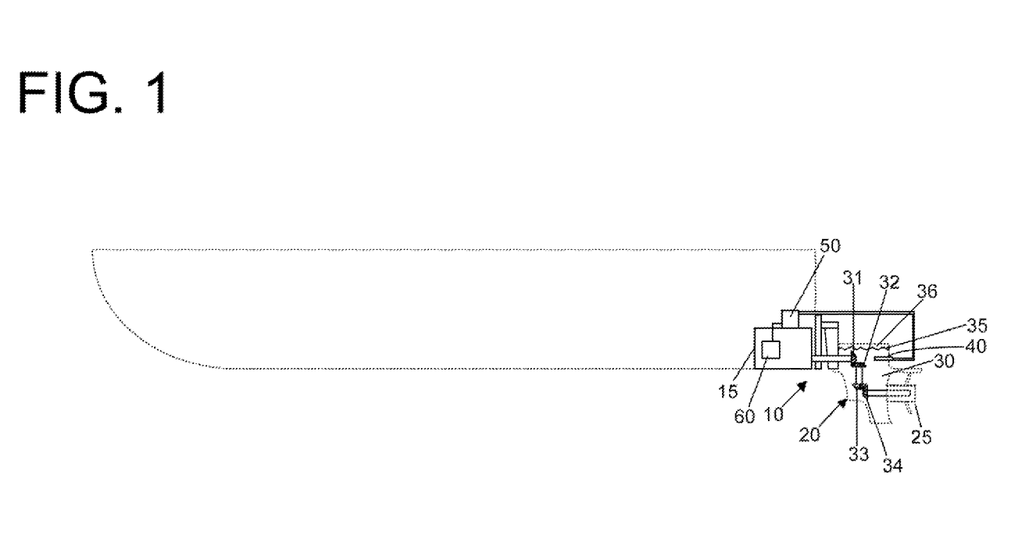
FIG. 1 depicts a boat and a marine powertrain, with an internal gear casing shown, according to one embodiment.
Figure 2:
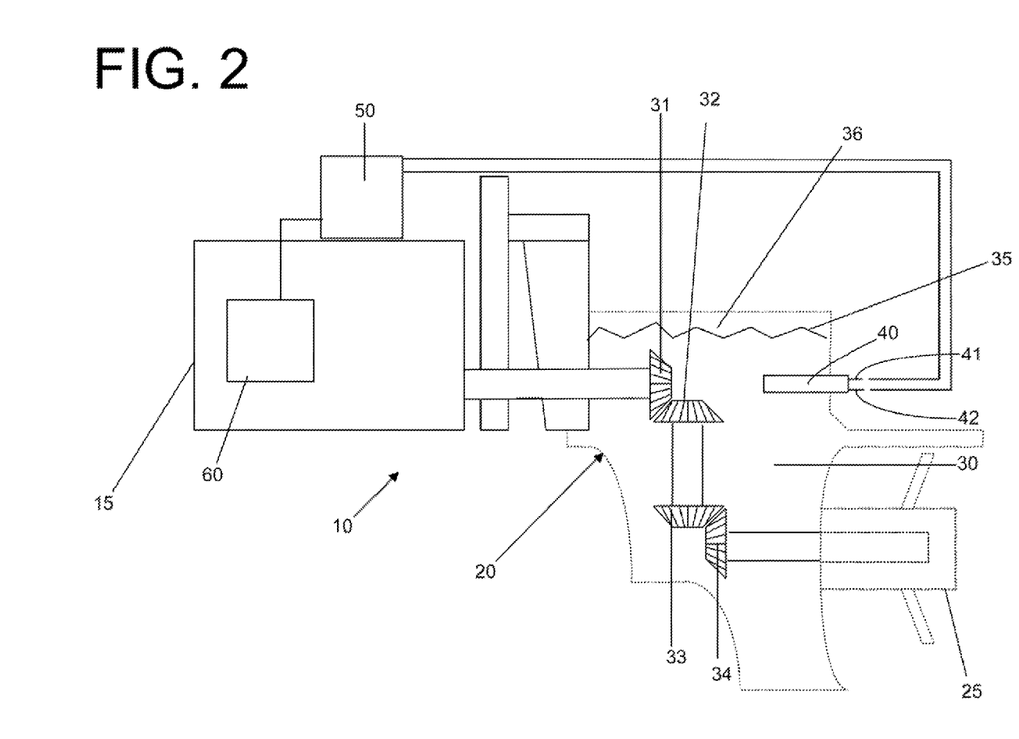
FIG. 2 depicts a marine powertrain, with an internal gear casing shown, according to one embodiment.
Figure 3:
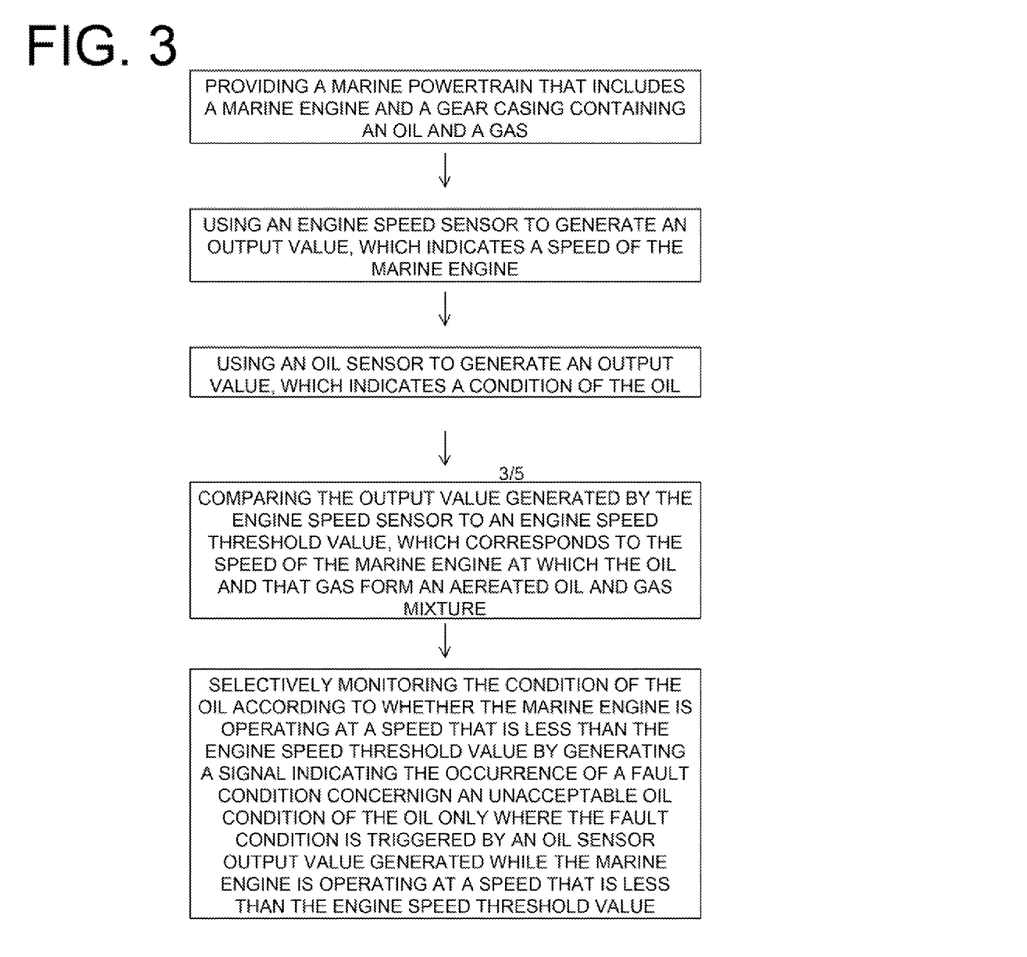
FIG. 3 depicts a method for monitoring oil condition according to one embodiment.
Figure 4:
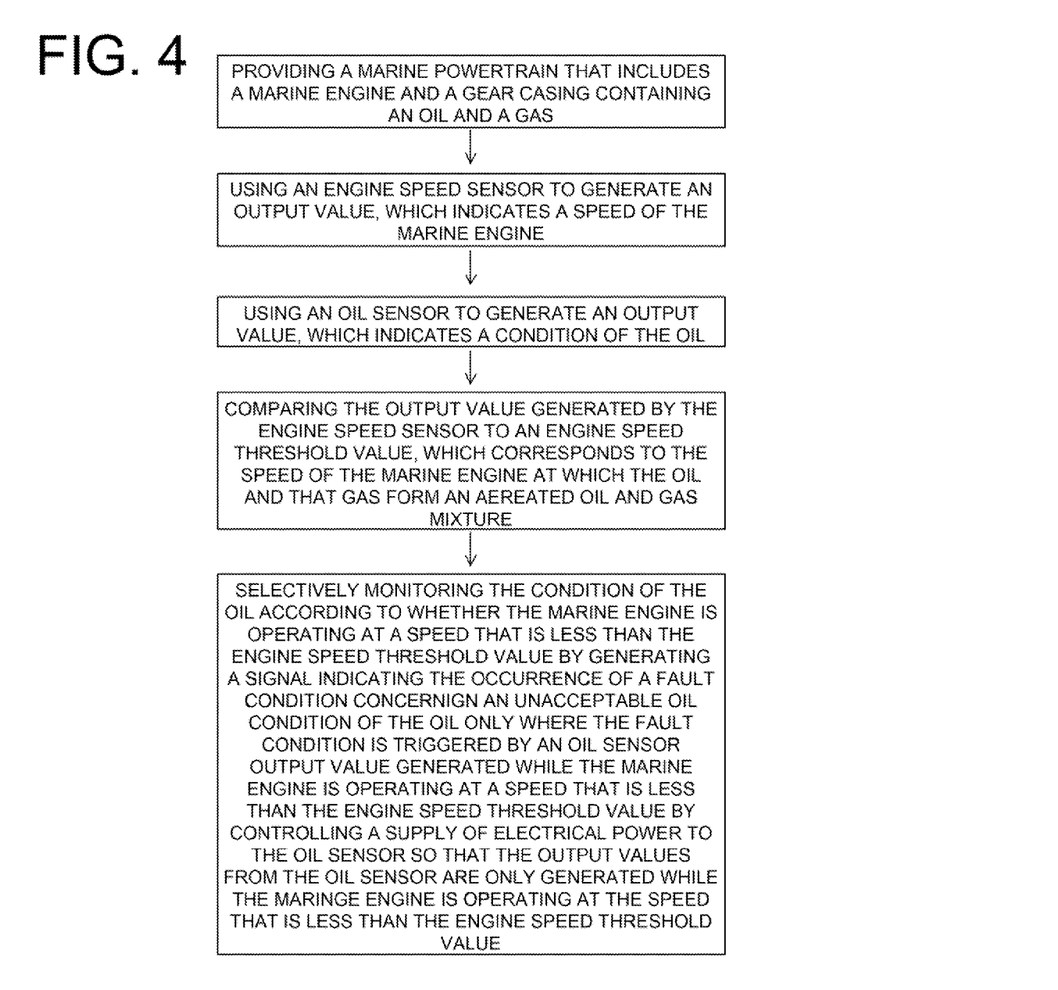
FIG. 4 depicts a method for monitoring oil condition according to one embodiment.
Figure 5:
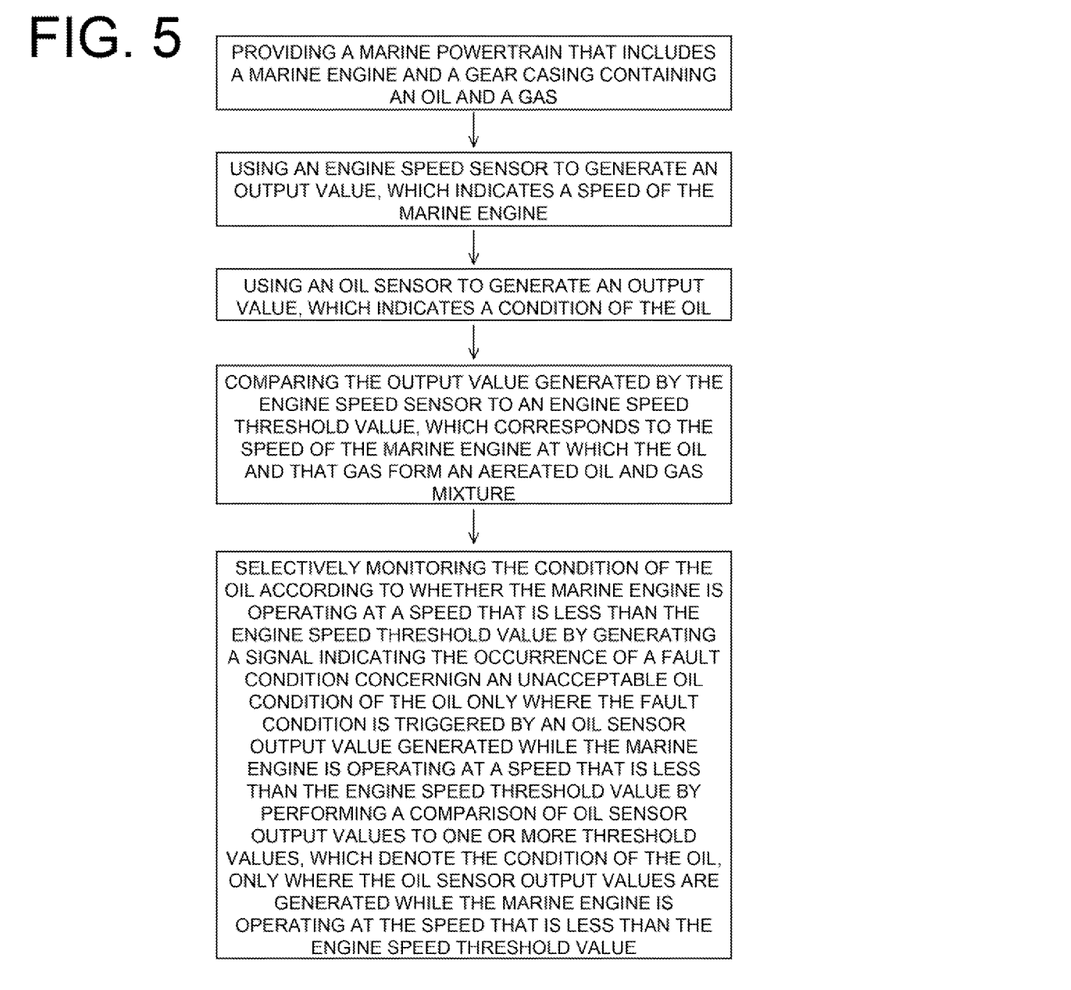
FIG. 5 depicts a method for monitoring oil condition according to one embodiment.

FIGS. 1 and 2 depict a marine powertrain 10 according to one embodiment of the present invention. In the present embodiment the marine powertrain 10 is a stern drive, however, in alternative embodiments the marine powertrain 10 may be provided with alternative configurations, such as, for example, as an outboard or an inboard marine powertrain configuration.

As shown therein, the marine powertrain 10 is provided with an outdrive 20, which is provided with a marine propulsion device 25. The propulsion device may be a propeller or any other suitable device. Also shown, the marine powertrain 10 is provided with a marine engine 15 or motor.

In the embodiment depicted in FIGS. 1 and 2, the outdrive 20 also includes a gear casing 30. The gear casing 30 contains gears, such as, for example 31, 32, 33, and 34, which transfer torque generated by the marine engine 15 of the marine powertrain 10 to the marine propulsion device 11. Also, shown the gear casing 30 contains lubricating oil 35, which lubricates the gears 31, 32, 33, and 34. As preferably shown, the gear casing 30 may be partially filled with oil 35, whereby the gear casing 30 also contains a gas 36, such as air.

In the present embodiment, the outdrive 20 is also provided with an oil sensor 40, which is shown connected to one or more electronics 50. The oil sensor 40 generates an output value, which indicates the oil condition. Although in the present embodiment, the oil sensor 40 is preferably in the form of a capacitance sensor, the oil sensor 40 may also take the form of other sensors, including, but not limited to, optical sensors, electrical resistance based sensors, or resonance sensors, for example, tuning fork resonance sensors.

In the preferred embodiment, wherein the oil sensor 40 is in the form of a capacitance sensor, those of ordinary skill in the art will appreciate that the dielectric constant of the oil varies according to the condition of the oil 35, including the quality and level of the oil 35. Those of ordinary skill in the art will also appreciate that dielectric constant of the oil 35 may be reflected in the voltage output or an oscillating output current frequency, which vary according to the dielectric constant of the oil 35. Those of ordinary skill in the art will appreciate that the voltage output or current frequency may be monitored to determine the condition of the oil 25. By way of example, and not limitation, in the case of a voltage output, oil contaminated with water may be indicated by a relatively high voltage output and a dangerously low level of oil 35 may be indicated by a relatively low voltage output, relative to a normative base line voltage output indicative of oil of an acceptable condition.

Those of ordinary skill in the art will appreciate that the condition of the oil 35 may change due to a number of factors, including, for example, oxidation, hydrolysis, thermal extremes, the introduction of wear components, or contamination, including by water. Empirical analysis or known reference tables may be used to determine which particular output values correspond to oil of an acceptable condition and which particular oil output values correspond to oil of an inacceptable condition. This information may be compiled, such as, for example, in a look up table, which may take the form of software or data, for example, which is accessed by or installed on one or more electronics 50. For example, the one or more electronics 50 may access this information, compare it to a current oil sensor output value and determine whether a current oil sensor output denotes a problem with the oil condition.

Since, the particular oil sensor output values that correspond to oil of an acceptable and inacceptable condition, will depend on a number of factors, including, for example, the marine powertrain type and type of oil 35, in one embodiment of the present invention, the output values that denote oil of an acceptable and inacceptable condition may be established and reset each time the oil is changed by performing an analysis when the oil 35 is fresh. Used oil located in the gear casing may be removed and new oil may be introduced. Since at such a point in time, the condition of the oil 35 should be optimal, one or more output values from the oil sensor 40 may be used to establish a normative baseline corresponding to oil of an acceptable condition. Based on an established normative baseline, one or more threshold values, which denote oil 35 of an unacceptable condition, may be established by adding and subtracting from this normative baseline. For example, in the case of a capacitance type oil sensor, which provides a voltage output that varies according to the dielectric constant, an upper threshold value denoting contamination with water may be determined and a lower threshold value denoting a dangerously low level of oil may be determined. The particular value added or subtracted may be established in a number of ways, including via known reference tables or empirical analysis.

Turning now again to FIGS. 1 and 2, the marine engine 15 or motor of the marine powertrain 10 is shown provided with an engine speed sensor 60, which is shown connected to the one or more electronics 50. The engine speed sensor 60 generates an output value, which indicates the speed of the marine engine 15. While the engine speed sensor 60 may take the form of a magnetic based sensor, those of ordinary skill in the art will appreciate that it is within the scope of the present embodiment to utilize any type of engine speed sensor 60. By way of example, and not limitation, the position of the throttle may be monitored to indicate engine speed as well or the speed of any component in the transmission system may be monitored to indicate engine speed as well.

According to one aspect of the present embodiment, the engine speed sensor 60 is configured to monitor the speed of the marine engine 15, such as, for example, the revolutions per minute of the marine engine 15. According to another aspect of the present embodiment, the engine speed sensor 60 may be used to determine an engine speed threshold value, which denotes the speed of the marine engine 15 at which the oil 35 and gas 36 form an oil and aerated gas mixture. While the engine speed sensor 60 of the present embodiment may be used in determining the engine speed threshold value, in alternative embodiments, the engine speed threshold value may be established in a number of ways, including, for example, and not limitation, by conservatively selecting an engine speed threshold whereat mixing will not occur, including, an idle speed, for example.

Those of ordinary skill in the art will appreciate that engine speed threshold value may depend on a number of factors, including the marine powertrain type and type of oil 35. Accordingly, in one embodiment of the present invention, the engine speed threshold value may be established and reset each time the oil 35 is changed by performing an analysis when the oil 35 is fresh. Since at such a point in time, it is known that the condition of the oil 35 is optimal, the output values from the oil sensor 40 may be used to establish the normative baseline for oil of an acceptable condition. The output values from the oil sensor 40 may then be monitored as the speed of the marine engine 15 is increased. The engine speed threshold value may be established by determining the speed of the marine engine 15 at which the oil sensor 40 begins to provide output values, which deviate from the normative baseline for oil of an acceptable condition to an extent which materially affects the ability of the output values from the oil sensor 40 to accurately indicate the condition of the oil 35. This information may be stored as data, for example, which is accessed by or installed on the one or more electronics 50. For example, the one or more electronics 50 may access this information and compare it to a current speed value of the marine engine 15 to determine whether the marine engine 15 is operating at a speed that exceeds the engine speed threshold value.

Turning again to FIGS. 1 and 2, the one or more electronics 50 are shown connected to the oil sensor 40 and the engine speed sensor 60. According to one aspect of the present embodiment, the one or more electronics 50 monitor the condition of the oil 35 using the output provided by the oil sensor 40. According to another aspect of the present embodiment, the one or more electronics 50 monitor the condition of the oil 35 using the one or more threshold values which denote oil of an unacceptable condition. According to yet another aspect of the present embodiment, the one or more electronics 50 monitor the condition of the oil 35 by comparing the output value provided by the oil sensor 40 to the one or threshold values, which denote oil 35 of an unacceptable condition.

According to another aspect of the present embodiment, the one or more electronics 50 selectively monitor the condition of the oil 35 according to whether the marine engine 15 is operating at a speed that is less than the engine speed threshold value. According to yet another aspect of the present embodiment, the one or more electronics 50 selectively monitor the condition of the oil 35 when the marine engine 15 is operating at a speed that is less than the engine speed threshold value. The selective monitoring of the present embodiment may take a variety of forms, including, using the one or more electronics to control a supply of electrical power to the oil sensor so that the output values from the oil sensor are only generated while the marine engine 15 is operating at a speed that is less than the engine speed threshold value, performing a comparison of oil sensor output values to the one or more threshold values only where the oil sensor output values are generated while the marine engine 15 is operating at a speed that is less than the engine speed threshold value, or generating a signal indicating the occurrence of a fault condition concerning an unacceptable condition of the oil only where the fault condition is triggered by an oil sensor output value generated while the marine engine 15 is operating at a speed that is less than the engine speed threshold value.

Although specific embodiments of, and examples for, the invention are described herein for illustrative purposes, various equivalent modifications are possible within the scope of the invention, as those skilled in the relevant art will recognize. For example, while the principals of the invention may be undertaken by the one or more electronics 50, in combination with the oil sensor 40 and the engine speed sensor 60, the principals of the present invention may be manually performed, to various degrees, using the measurement values supplied by the oil sensor 40 and the engine speed sensor 60. Those of ordinary skill in the art will appreciate that the aspects of the present invention may be embodied in computer program product comprising computer usable medium including executable code.

Furthermore, the detailed descriptions of the above embodiments are not exhaustive descriptions of all embodiments contemplated by the inventors to be within the scope of the invention. Persons skilled in the art will recognize that certain elements of the above-described embodiments may variously be combined or eliminated to create further embodiments, and such further embodiments fall within the scope and teachings of the invention. It will also be apparent to those of ordinary skill in the art that the above-described embodiments may be combined in whole or in part to create additional embodiments within the scope and teachings of the invention. Accordingly, the scope of the invention is determined from the appended claims and equivalents thereof.

We claim:

1. A system for monitoring oil condition, comprising:
   a marine powertrain provided with a marine engine and a gear casing containing an oil and a gas;
   an engine speed sensor that generates an output value, which indicates a speed of the marine engine;
   an oil sensor that generates an output value, which indicates a condition of the oil;
   one or more electronics, which:
     receive the output value from the oil sensor;
     receive the output value from the engine speed sensor; and
     selectively monitor the condition of the oil according to whether the marine engine is operating at a speed that is less than an engine speed threshold value, which denotes a speed of the marine engine at which the oil and the gas form an aerated oil and gas mixture, by generating a signal indicating the occurrence of a fault condition concerning an unacceptable condition of the oil only where the fault condition is triggered by an oil sensor output value generated while the marine engine is operating at a speed that is less than the engine speed threshold value.

2. The system for monitoring oil condition according to claim 1, wherein the one or more electronics control a supply of electrical power to the oil sensor so that output values from the oil sensor are only generated while the marine engine is operating at the speed that is less than the engine speed threshold value.

3. The system for monitoring oil condition according to claim 1, wherein the one or more electronics perform a comparison of oil sensor output values to one or more threshold values, which denote the condition of the oil, only where the oil sensor output values are generated while the marine engine is operating at a speed that is less than the engine speed threshold value.

4. The system for monitoring oil condition according to claim 1, wherein the oil sensor is a capacitance sensor, an electrical resistance sensor, a resonance sensor, or an optical sensor.

5. A method for monitoring oil condition, comprising:
providing a marine powertrain that includes a marine engine and a gear casing containing an oil and a gas;
using an engine speed sensor to generate an output value, which indicates a speed of the marine engine;
using an oil sensor to generate an output value, which indicates a condition of the oil;
comparing the output value generated by the engine speed sensor to an engine speed threshold value, which corresponds to a speed of the marine engine at which the oil and the gas form an aerated oil and gas mixture;
selectively monitoring the condition of the oil according to whether the marine engine is operating at a speed that is less than the engine speed threshold value by generating a signal indicating the occurrence of a fault condition concerning an unacceptable condition of the oil only where the fault condition is triggered by an oil sensor output value generated while the marine engine is operating at a speed that is less than the engine speed threshold value.

6. The method for monitoring oil condition according to claim 5, wherein the step of selectively monitoring the condition of the oil according to whether the marine engine is operating at a speed that is less than the engine speed threshold value by generating the signal indicating the occurrence of the fault condition concerning the unacceptable condition of the oil only where the fault condition is triggered by the oil sensor output value generated while the marine engine is operating at the speed that is less than the engine speed threshold value includes the step of controlling a supply of electrical power to the oil sensor so that output values from the oil sensor are only generated while the marine engine is operating at the speed that is less than the engine speed threshold value.

7. The method for monitoring oil condition according to claim 5, wherein the step of selectively monitoring the condition of the oil according to whether the marine engine is operating at a speed that is less than the engine speed threshold value by generating the signal indicating the occurrence of the fault condition concerning the unacceptable condition of the oil only where the fault condition is triggered by the oil sensor output value generated while the marine engine is operating at the speed that is less than the engine speed threshold value includes the step of performing a comparison of oil sensor output values to one or more threshold values, which denote the condition of the oil, only where the oil sensor output values are generated while the marine engine is operating at the speed that is less than the engine speed threshold value.

8. The method for monitoring oil condition according to claim 5, wherein the oil sensor is a capacitance sensor, an electrical resistance sensor, a resonance sensor, or an optical sensor.

9. The method for monitoring oil condition according to claim 5, wherein the engine speed threshold value is stored on one or more electronics, whereby the stored engine speed threshold value may be reset each time the oil is changed.

10. The method for monitoring oil condition according to claim 6, wherein:
the step of selectively monitoring the condition of the oil according to whether the marine engine is operating at a speed that is less than the engine speed threshold value occurs by performing a comparison of oil sensor output values to one or more threshold values; and
the one or more threshold values are stored on one or more electronics, whereby the stored one or more threshold values may be reset each time the oil is changed.

11. A computer program product comprising computer usable medium including executable code for executing a process for monitoring oil condition in a marine powertrain, which includes a marine engine and a gear casing containing an oil and a gas, an engine speed sensor that generates an output value, which indicates a speed of the marine engine, and an oil sensor, which generates an output value indicating a condition of the oil, the process comprising the steps of:
using one or more electronics to compare the output value generated by the engine speed sensor to an engine speed threshold value, which corresponds to a speed of the marine engine at which the oil and the gas form an aerated oil and gas mixture; and using the one or more electronics to selectively monitor the condition of the oil according to whether the marine engine is operating at a speed that is less than the engine speed threshold value by generating a signal indicating the occurrence of a fault condition concerning an unacceptable condition of the oil only where the fault condition is triggered by an oil sensor output value generated while the marine engine is operating at a speed that is less than the engine speed threshold value.

12. The computer program product according to claim 11, wherein the step of using the one or more electronics to selectively monitor the condition of the oil according to whether the marine engine is operating at the speed that is less than the engine speed threshold value by generating the signal indicating the occurrence of the fault condition concerning the unacceptable condition of the oil only where the fault condition is triggered by the oil sensor output value generated while the marine engine is operating at the speed that is less than the engine speed threshold value includes the step of controlling a supply of electrical power to the oil sensor so that output values from the oil sensor are only generated while the marine engine is operating at the speed that is less than the engine speed threshold value.

13. The computer program product according to claim 11, wherein the step of using the one or more electronics to selectively monitor the condition of the oil according to whether the marine engine is operating at the speed that is less than the engine speed threshold value by generating the signal indicating the occurrence of the fault condition concerning the unacceptable condition of the oil only where the fault condition is triggered by the oil sensor output value generated while the marine engine is operating at the speed that is less than the engine speed threshold value includes the step of performing a comparison of oil sensor output values to one or more threshold values, which denote the condition of the oil, only where the oil sensor output values are generated while the marine engine is operating at the speed that is less than the engine speed threshold value.

14. The computer program product according to claim 11, wherein the oil sensor is a capacitance sensor, an electrical resistance sensor, a resonance sensor, or an optical sensor.

15. The computer program product according to claim 11, wherein the engine speed threshold value is stored on one or more electronics, whereby the stored engine speed threshold value may be reset each time the oil is changed.

16. The computer program product according to claim 11, wherein:
the step of selectively monitoring the condition of the oil according to whether the marine engine is operating at a speed that is less than the engine speed threshold value occurs by performing a comparison of oil sensor output values to one or more threshold values; and
the one or more threshold values are stored on one or more electronics, whereby the stored one or more threshold values may be reset each time the oil is changed.

\* \* \* \* \*